United States Patent
Srimathveeravalli et al.

(10) Patent No.: US 11,596,788 B2
(45) Date of Patent: Mar. 7, 2023

(54) SYSTEM, METHOD AND COMPUTER-ACCESSIBLE MEDIUM FOR TREATING CIRCULATING TUMOR CELLS IN THE BLOOD STREAM

(71) Applicant: MEMORIAL SLOAN-KETTERING CANCER CENTER, New York, NY (US)

(72) Inventors: Govindarajan Srimathveeravalli, Kew Gardens, NY (US); Stephen Barnett Solomon, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 531 days.

(21) Appl. No.: 16/082,199

(22) PCT Filed: Mar. 2, 2017

(86) PCT No.: PCT/US2017/020544
§ 371 (c)(1),
(2) Date: Sep. 4, 2018

(87) PCT Pub. No.: WO2017/151987
PCT Pub. Date: Sep. 8, 2017

(65) Prior Publication Data
US 2020/0289819 A1    Sep. 17, 2020

Related U.S. Application Data

(60) Provisional application No. 62/302,532, filed on Mar. 2, 2016.

(51) Int. Cl.
*A61N 1/36* (2006.01)
*A61M 1/36* (2006.01)
(Continued)

(52) U.S. Cl.
CPC ........... *A61N 1/36002* (2017.08); *A61M 1/36* (2013.01); *A61M 1/3601* (2014.02);
(Continued)

(58) Field of Classification Search
CPC .. A61N 1/36002; A61N 1/0412; A61N 1/327; A61N 1/40; A61M 60/50;
(Continued)

(56) References Cited

U.S. PATENT DOCUMENTS

| 3,737,251 A | 6/1973 | Berman et al. |
| 5,011,472 A | 4/1991 | Aebischer et al. |

(Continued)

FOREIGN PATENT DOCUMENTS

| DE | 19849787 C1 * | 2/2000 | ............ A61M 1/16 |
| WO | WO-9641292 A1 * | 12/1996 | ............ G16H 20/40 |
| WO | WO 2016/175913 | 11/2016 | |

OTHER PUBLICATIONS

"Port." Merriam-Webster.com Dictionary, Merriam-Webster, https://www.merriam-webster.com/dictionary/port. Accessed Feb. 4, 2021. (Year: 2021).*

(Continued)

*Primary Examiner* — Tatyana Zalukaeva
*Assistant Examiner* — Ilya Y Treyger
(74) *Attorney, Agent, or Firm* — Hunton Andrews Kurth LLP

(57) ABSTRACT

An exemplary apparatus, can include, for example, a circulating tumor cell (CTC) treatment arrangement, a pump arrangement configured to circulate a fluid through the CTC treatment arrangement, and an electric field generator electrically connected to the CTC treatment arrangement, and configured to apply an electric field to the fluid circulating through the CTC treatment arrangement. The pump arrangement can be a peristaltic pump, which can be configured to (Continued)

continuously circulate the fluid through the CTC treatment arrangement. According to another exemplary embodiment of the present disclosure, method, system and computer-accessible medium can be provided for killing at least one circulating tumor cell (CTC). Using such exemplary embodiment, blood can be pumped from a body of a patient to an electroporation chamber inside of a CTC treatment arrangement. An electric field can be applied to the blood located in the electroporation chamber in order to kill the CTC. The electric field-applied blood can be pumped back into the body.

27 Claims, 13 Drawing Sheets

(51) Int. Cl.
- A61N 1/04 (2006.01)
- A61N 1/32 (2006.01)
- A61N 1/40 (2006.01)
- A61M 60/279 (2021.01)
- A61M 60/441 (2021.01)
- A61M 60/36 (2021.01)
- A61M 60/113 (2021.01)

(52) U.S. Cl.
CPC ........ A61M 1/3659 (2014.02); A61M 60/113 (2021.01); A61M 60/279 (2021.01); A61M 60/36 (2021.01); A61M 60/441 (2021.01); A61N 1/0412 (2013.01); A61N 1/327 (2013.01); A61N 1/40 (2013.01)

(58) Field of Classification Search
CPC .............. A61M 60/279; A61M 1/3659; A61M 1/3601; A61M 1/36; A61M 5/142
See application file for complete search history.

(56) References Cited

U.S. PATENT DOCUMENTS

| | | | |
|---|---|---|---|
| 5,137,817 A * | 8/1992 | Busta | A61N 1/042 435/173.6 |
| 5,139,684 A | 8/1992 | Kaali et al. | |
| 5,705,018 A | 1/1998 | Hartley | |
| 6,969,604 B1 * | 11/2005 | Yakovenko | C12M 35/02 204/403.01 |
| 2002/0138034 A1 | 9/2002 | Derek et al. | |
| 2005/0096584 A1 * | 5/2005 | Ferek-Petric | A61N 1/325 604/20 |
| 2006/0108229 A1 | 5/2006 | Walters et al. | |
| 2007/0231873 A1 * | 10/2007 | Ragsdale | C12N 13/00 435/173.6 |
| 2011/0244443 A1 * | 10/2011 | van Rijn | G01N 33/57492 435/2 |
| 2012/0109122 A1 | 5/2012 | Arena et al. | |
| 2013/0131423 A1 | 5/2013 | Wang et al. | |
| 2013/0178834 A1 | 7/2013 | Greenberg et al. | |
| 2014/0014226 A1 | 1/2014 | Green et al. | |
| 2014/0358066 A1 * | 12/2014 | Nuccitelli | A61K 39/39558 604/20 |

OTHER PUBLICATIONS

"Chamber." Merriam-Webster.com Dictionary, Merriam-Webster, https://www.merriam-webster.com/dictionary/chamber. Accessed Feb. 4, 2021. (Year: 2021).*
Lin et al., Electroporation microchips for continuous gene transfection, Sensors & Actuators B, 79 (2001), 1, 7-14. (Year: 2001).*
Shrirao (Anil B. Shrirao, High aspect ratio electrodes for high yield electroporation of cells, electrical engineering PhD dissertation, New Jersey Institute of Technology, Aug. 2012) (Year: 2012).*
Jorge Nieva et al High-definition imaging of circulating tumor cells and associated cellular events in non-small cell lung cancer patients: a longitudinal analysis 2012 Phys. Biol. 9 016004). (Year: 2012).*
Justin Stebbing The Efficacy of Lapatinib in Metastatic Breast Cancer with HER2 Non-Amplified Primary Tumors and EGFR Positive Circulating Tumor Cells: A Proof-of-Concept Study, PLOS ONE, May 2013| Volume 8| Issue 5| e62543) (Year: 2013).*
Zihua Zeng, A cancer cell-activatable aptamer-reporter system for one-step assay of circulating tumor cell, Mol Ther Nucleic Acids, 2014, Aug. 12;3(8):e184. doi: 10.1038/mtna.2014.36) (Year: 2014).*
Stefanie Heinemann, Brigitte Biesinger, Bernhard Fleckenstein, and Jens-Christian Albrecht, NFKB Signaling is Induced by the Oncoprotein Tio through Direct Interaction with TRAF6, The Journal of Biological Chemistry vol. 281, No. 13, pp. 8565-8572, Mar. 31, 2006) (Year: 2006).*
Konstantin Cesnulevicius, Expansion, differentiation and transfection of ventral mesencephalic progenitor cells—characterization in vitro and after implantation in animal model of Parkinson's disease, Oct. 20, 2006, University of Veterinary Medicine Hannover . (Year: 2006).*
John Roche. "Introducing electric fields". Physics Education, vol. 51, Numbers. (Year: 2016).*
National Cancer Institute, [from the Internet] http://web.archive.org/web/20111210111554/http://www.cancer.gov/, Dec. 9, 2011.
Ali, D. et al., "Treatment of the primary tumor in breast cancer patients with synchronous metastases," Annals of Oncology, vol. 22, pp. 9-16, 2011.
Harvard Apparatus, [from the Internet] http://web.archive.org/web/20111102144657/http://www.harvardapparatus.com:80/webapp/wcs/stores/servlet/catalog_11051_10001_-1_HAI, pp. 1-4, Nov. 14, 2011.
Pumps & Systems, [from the Internet] https://web.archive.org/web/20111031043133/http://www.pump-zone.com:80/, pp. 1-8, Nov. 14, 2011.
First Ten Angstroms, https://web.archive.org/web/20110904054502/http://www.firsttenangstroms.com:80/, Nov. 14, 2011.
Jurgons, R. et al. "Drug loaded magnetic nanoparticles for cancer therapy," Journal of Physics: Condensed Matter, vol. 18, pp. S2893-S2902, Sep. 2006.
Wang, Shutao et al. "Highly efficient capture of circulating tumor cells by using nanostructured silicon substrates with integrated chaotic micromixers," Angew. Chem. Int. Ed., vol. 50, pp. 3084-3088, 2011.
Bao, N. et al. "A microfluidic electroporation device for cell lysis," Integr. Biol., vol. 2, pp. 113-120, Apr. 2004.
Lu, Hang et al. "A Microfluidic electroporation Device for Cell Lysis," Lab Chip, vol. 5, pp. 23-29, 2005.
Fox, M.B. et al. "Electroporation of cells in microfluidic devices: A review," Anal Bioanal Chem, vol. 385, pp. 474-485, 2006.
Weaver, James C., "Electroporation: A general phenomenon for manipulating cells and tissues," Journal of Cellular Biochemistry, vol. 51, pp. 426-435, 1993.
Bertacchini, Claudio C. et al., "Design of an irreversible electroporation system for clinical use," vol. 6, No. 4, pp. 313-320, Aug. 2007.
Pump System Inc. [From the Internet] https//web.archive.org/web/20111115003559/www.syringepump.com/index.php, pp. 1-2, Dec. 9, 2011.
Solid State Technology, [From the Internet] http://www.electroiq.com/articles/stm/2008/02/bbiomedical-applications-using-magnetic-nanoparticles-b.html, pp. 1-9, Dec. 9, 2011.
Stott, Shannon L. et al. "Isolation of circulating tumor cells using a microvortex-generating herringbone-chip," Proceedings of the National Academy of Sciences of the United States of America, vol. 107, No. 43, pp. 18392-18397, Oct. 26, 2010.
Misra, Madhukar, "The basics of hemodialysis equipment," Hemodialysis International, vol. 9, pp. 30-36, Jan. 2005.
Kinetics of Microbial Inactivation for Alternative Food Processing Technologies, Pulsed Electric Fields, [from the Internet] http://www.fda.gov/food/scienceresearch/researchareas/safepracticesforfoodproc esses/ucm101662.htm, Jun. 2, 2000.
Bao, Ning et al. "A microfluidic electroporation device for cell lysis," Electrophoresis,vol. 29, pp. 2939-2944, 2008.
International Search Report for International Application No. PCT/US2017/020544 dated May 22, 2017.

(56) References Cited

OTHER PUBLICATIONS

International Written Opinion for International Application No. PCT/US2017/020544 dated May 22, 2017.

* cited by examiner

SYSTEM, METHOD AND COMPUTER-ACCESSIBLE MEDIUM FOR TREATING CIRCULATING TUMOR CELLS IN THE BLOOD STREAM

CROSS REFERENCE TO RELATED APPLICATION(S)

The present application relates to and claims priority from International Patent Application PCT/US2017/020544, filed Mar. 2, 2017 published as International Publication No. WO 2017/151987 on Sep. 8, 2017, and from U.S. Provisional Patent Application No. 62/302,532, filed on Mar. 2, 2016, the entire disclosures of which are incorporated herein by reference.

FIELD OF THE DISCLOSURE

The present disclosure relates generally to blood stream circulation, and more specifically to exemplary embodiments of an exemplary system, method and computer-accessible medium for circulating tumor cells in the blood stream.

BACKGROUND INFORMATION

Metastasis cancer is a group of cancer cells that spread from the primary tumor site to other parts of the body such as liver, lungs, brain and bone. These circulating tumor cells (e.g., "CTC"s) can travel through lymphatic fluid or the bloodstream to other tissue where they separate out from the primary tumor tissue. However, these cells first have to break into the bloodstream that can carry them to travel anywhere inside the body, then they have to accumulate at certain locations and penetrate into tissue to start a new tumor. Metastasis cancer usually requires more difficult treatment than the primary tumor because these cancer cells become more aggressive. According to the American Cancer Society, a 5 years survival rate of metastasis cancer can be about 5% to about 27%. (See, e.g., Reference 1). Thus a large number of people die because of metastasis cancer.

The process by which CTCs travel to other sites can develop from virtually any type of metastatic cancer. Metastasis involves the following steps:
1. Local invasion: Cancer cells invade nearby tissues.
2. Intravasation: Cancer cells invade and move through nearby lymph or blood vessels.
3. Circulation: Cancer cells move through the bloodstream or lymphatic fluid into other parts of the body.
4. Extravasation/Arrest: Cancer cells accumulate at a capillary and start invading nearby tissues.
5. Proliferation: These cells proliferate and develop into a secondary tumor called micrometastases.
6. Angiogenesis: Micrometastases release chemicals causing the growth of new blood vessels to obtain the oxygen and nutrients needed for the growth of tumors. There are several clinical treatments for the first two steps and the last two steps such as chemo/immunotherapy, endocrine therapy, biological therapy and radiation/surgery/intervention. (See, e.g., Reference 2).

Thus, it may be beneficial to provide an exemplary system, method and computer-accessible medium for selectively targeting CTCs in a sample of blood that can eliminate CTCs externally in a large volume of blood, while not damaging the blood stream, in order to treat CTCs that remain in the blood stream after clinical treatments to prevent primary cancer patients from getting metastatic cancers, as well as to avoid, reduce and/or eliminate the deficiencies and issues of the prior systems, devices and methods.

SUMMARY OF EXEMPLARY EMBODIMENTS

An exemplary apparatus, can include, for example, a circulating tumor cell ("CTC") treatment arrangement, a pump arrangement configured to circulate a fluid through the CTC treatment arrangement, and an electric field generator electrically connected to the CTC treatment arrangement, and configured to apply an electric field to the fluid circulating through the CTC treatment arrangement. The pump arrangement can be a peristaltic pump, which can be configured to continuously circulate the fluid through the CTC treatment arrangement.

In some exemplary embodiments of the present disclosure, the fluid can be blood from a patient. The electric field can be configured to kill a CTC(s) in the fluid. In certain exemplary embodiments of the present disclosure, the electric field can include a plurality of micro pulses. The CTC treatment arrangement can include an electroporation chamber(s). A plurality of electrodes can be positioned inside of the electroporation chamber and can be electrically connected to the electric field generator. The CTC treatment arrangement can include an input port and an output port. In some exemplary embodiments of the present disclosure, a first tube can be connected to the output port and can be configured to be inserted into a body of a patient, a second tube can be configured to be inserted into the body and can be connected to the pump arrangement, and a third tube can be connected to the pump arrangement and the input port of the CTC treatment arrangement In certain exemplary embodiments of the present disclosure, a method for killing a circulating tumor cell(s) ("CTC"), can include, for example, pumping blood from a body of a patient to an electroporation chamber inside of a CTC treatment arrangement, applying an electric field to the blood located in the electroporation chamber in order to kill the CTC(s), and pumping the electric field applied blood back into the body.

In some exemplary embodiments of the present disclosure, the pumping of the blood from the body and the pumping of the electric field applied blood into the body can be performed using a pumping arrangement, which can include a peristaltic pump. Further, blood from the body can be pumped to the electroporation chamber, a further electric field can be applied to the further blood located in the electroporation chamber in order to kill a further CTC(s), and/or the further electric field applied blood can be pumped back into the body. The electric field can include a plurality of micro pulses. The electroporation chamber can include a plurality of electrodes electrically connected to a field generator. Alternatively or in addition, the electroporation chamber can include an input port and an output port.

A further exemplary system, method and computer-accessible medium for killing a circulating tumor cell ("CTC") can be provided, in which, for example, blood can be pumped from a body of a patient to an electroporation chamber inside of a CTC treatment arrangement, an electric field can be applied to the blood located in the electroporation chamber in order to kill the CTC(s), and the blood to which electric field has been applied can be pumped back into the body.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
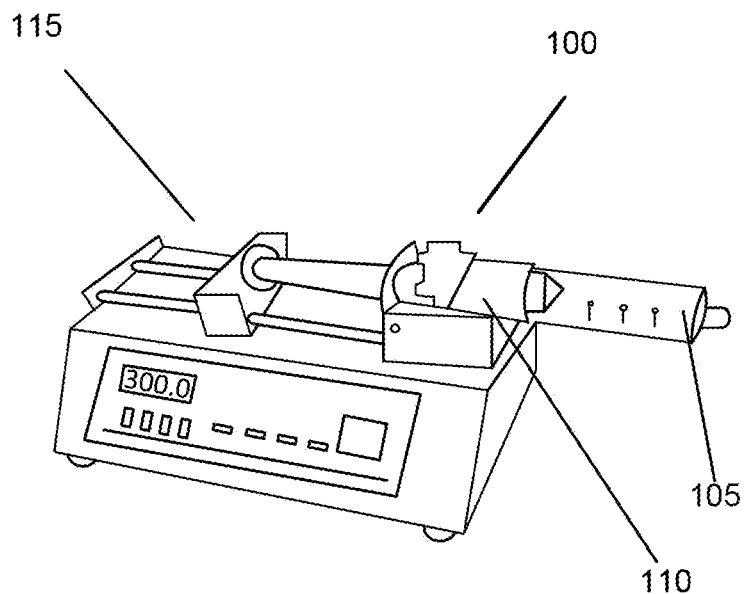
FIG. 1 is an exemplary image of an exemplary syringe pump according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium can affect CTCs in a sample of blood using a microfluidic device. This can expose the sample to an experimentally determined electric field for a specific duration of time. The exemplary system, method and computer-accessible medium, according to an exemplary embodiment of the present disclosure, can be utilized on larger volumes of fluid, for example, it can target CTCs within the blood stream. To achieve such result, an experimental study to extend existing results to meso scale volumes (e.g., approximately 0.4 ml) was performed using a commercial electroporation generator. The results of the exemplary experiment indicate that it can be possible to determine a combination of electric field strength and exposure time that can be used to target cancer cells without significantly damaging the constituents of the blood stream. Thus, the exemplary system, method and computer-accessible medium, according to an exemplary embodiment of the present disclosure, can be used to eliminate CTCs using this exemplary method within a large volume of blood while minimizing damage to the blood stream. The exemplary blood circulation system can be built by modeling the hemodialysis system which uses tubing and flow driven by a peristaltic pump. An engineered electroporation chamber can be used to replace the dialyzer component of a hemodialysis machine. The electroporation chamber can be connected with a power supply that can continuously provide stable electric field. The flow rate within the chamber can be adjusted to match values identified from the exemplary lab experiments.

In order to treat CTCs externally, two classes of problems can be considered. First, how is the blood removed and returned, and second, how can the CTCs be removed or attenuated in the blood. The exemplary questions can be categorized as Blood Circulation and Treatment Methods.

Exemplary blood circulation can be based on the following:
  Accuracy—How accurately can it transfer the desired volume of blood so that the correct magnitude of treatment can be used?
  Sterilization—How easy is it to keep clean?
  Cost—How much is the cost of using this method?
  Speed—How fast can the blood be safely transferred?

Exemplary treatment methods can be based on the following:
  Speed—Can this treatment process keep up with the blood circuit? What is the speed?
  Effectiveness—How effective is this treatment?
  Side effects—How bad are the side effects of this treatment?

FIG. 1 illustrates an exemplary photograph of an exemplary syringe pump apparatus 100 (e.g., a NE-300 mini syringe pump) according to an exemplary embodiment of the present disclosure. Such exemplary syringe pump apparatus 100 can connect q needle+tube configuration 105 to a syringe 110 mounted on a motor 115 that can facilitate the syringe 110 to infuse and withdraw blood. The syringe 110 can contain a reservoir where the volume of blood to be treated can lie. The syringe 110 can be used in conjunction with a vacuum. As the syringe 110 can be retracted, the vacuum can pull blood into the reservoir. When the syringe 110 is pushed, the back of the syringe 110 can create a pressure on the fluid inside the reservoir, pushing it out. There can be an intersection of tubing near the syringe 110 such that blood can be drawn from the patient in one tubing when the motor 115 can retract the syringe 110, and blood can be sent to the second tubing, leading back to the patient, when the motor 115 can push the syringe 110.

Some exemplary advantages of this design can be that it can be very precise, (e.g., accuracy of about <1% error) easy to clean/remove, and easily programmable.

Exemplary Peristaltic Pump

Peristaltic pumps operate on peristalsis, the principle in which many biological ducts, such as the digestive system and the ureter, convey their fluid contents by propulsion of internal fluid by propagating waves of muscular contraction in the surrounding tube wall. (See, e.g., Reference 21). For example, peristaltic pumps can include a compressible tube (e.g., or hose) held between a pumping rotor with rollers (e.g., or shoes), and the tube can be compressed periodically by rotation of the rotor, periodically occluding the tube and producing a flow of liquid in the tube. Furthermore, the ends of the tubes can be rigidly held adjacent to the associated pumping shoes so that the pump can operate symmetrically with the rotor being driven in either a pickup or delivery mode. (See, e.g., Reference 22).

The flow propelled by peristaltic pumps can move continuously. While the rollers rotate, the flow can move as continuous flow, and this continuous flow can barely cause air bubble in blood circulation system resulting in an embolism. Also, the only part contacted to blood can be its tube so that it can minimize the possibility of complications from the pumps. (See, e.g., Reference 4).

There can be several more advantages of peristaltic pumps. It can be inexpensive to maintain (e.g., lacking valves, seals and glands), and it can prevent regurgitation and siphoning without valves. (See, e.g., Reference 5). However, the accuracy can be in the range of about 1% to about 4% error. Despite the accurate control of flow rate, the accuracy can still be lower than the accuracy of an electromagnetic-driven pump. The peristaltic pump has a motor and a tube that can be subjected to heat, which can cause abrasion of those components, resulting in damage and potentially ceasing to function. As the peristaltic tube wears out from rotators (e.g., from frequent squeezing), the tube can develop holes that can lead to leaks. These leaks can cause the pump system to be much less efficient, and can cause a contamination if other chemicals enter into the tubes. (See, e.g., Reference 3).

Figure 2:
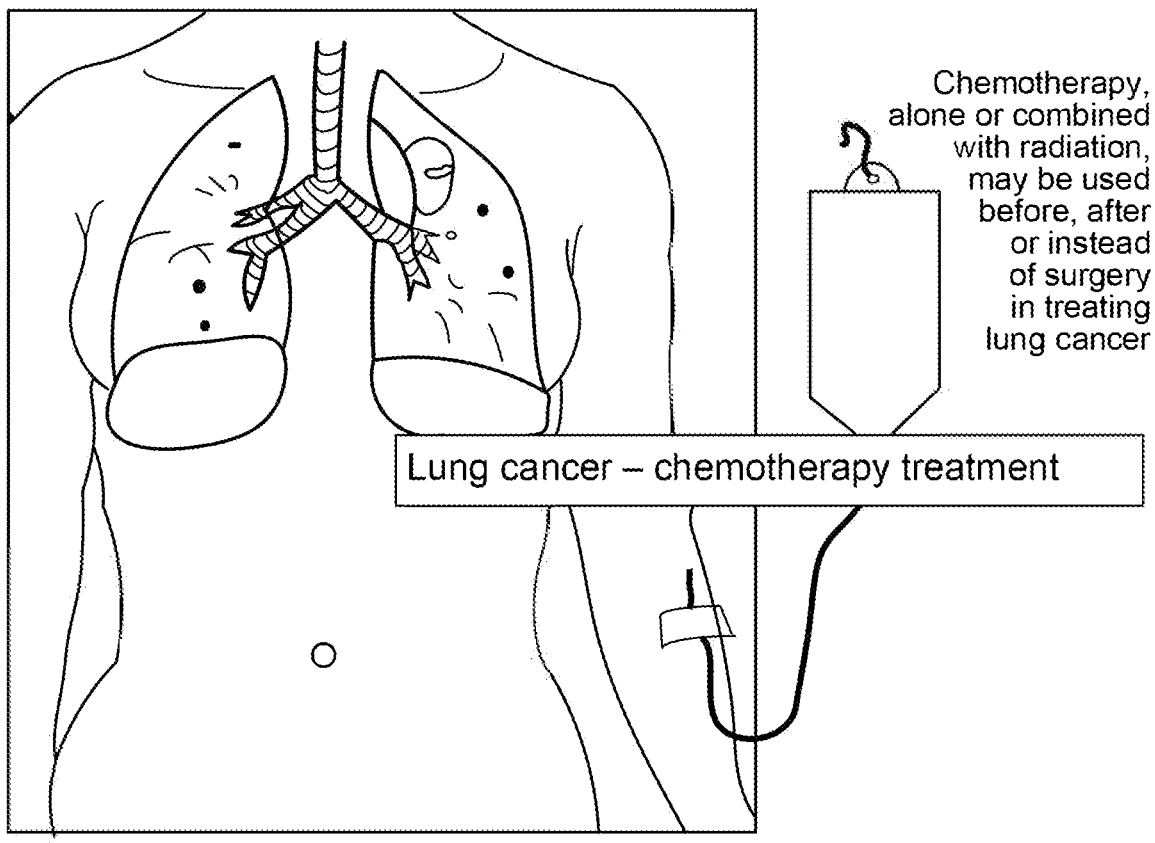
FIG. 2 is an exemplary image of an exemplary chemotherapy bag hooked into, or otherwise attached to, a patient according to an exemplary embodiment of the present disclosure.

Exemplary Treatment Methods—Removing Circulating Tumor Cells from the Blood Exemplary Chemotherapy Chemotherapy is a treatment process widely used in cases of primary tumor sites. It involves the use of chemicals which target cells that undergo fast mitosis. (See, e.g., image shown in FIG. 2). Chemotherapy kills tumor cells but also has the side effect of killing other rapidly dividing cells in the body such as bone marrow, hair, and cells in the digestive tract. Current chemotherapy methods include infusion of the drug into the bloodstream, local infusion, and even isolated infusion. The method of isolated infusion can be used in an exemplary system. In the isolated infusion, the blood flow in the tumor area can be stopped, and drugs can be delivered at a high concentration so that the whole body does not need to be exposed to the drug. In an exemplary case, the drug can be exposed to the circulating tumor cells outside the body so that the rest of the body does not need be exposed to such a high level.

Some of the exemplary advantages for using chemotherapy in treatment can be that it is a widely used and proven treatment process. Many clinics even determine how well the treatment of a primary tumor site by chemotherapy is proceeding by looking at the reduction in CTCs. It can also be easy to deliver it into the external blood circulation. Some problems can involve the issue of removing excess chemicals before returning it to the body. Chemotherapy also works best on cells that divide rapidly, thus if the CTC does not divide fast enough, it may not be affected as much, or may even be immune to the chemotherapy process. Further, Chemotherapy is usually used in the treatment process for primary tumor sites anyways, so it can be redundant to use it externally for CTCs (e.g., although, it may be more effective in specifically treating CTCs than in traditional chemotherapy).

Summary of Exemplary Chemotherapy

Speed—Cells can need some time for the drug to diffuse.
Effectiveness—Has been proven to work though not directly on CTCs.
Side effect—Almost nonexistent if the majority of the treatment is performed externally.

Exemplary Magnetic Nanoparticles

Figure 3:
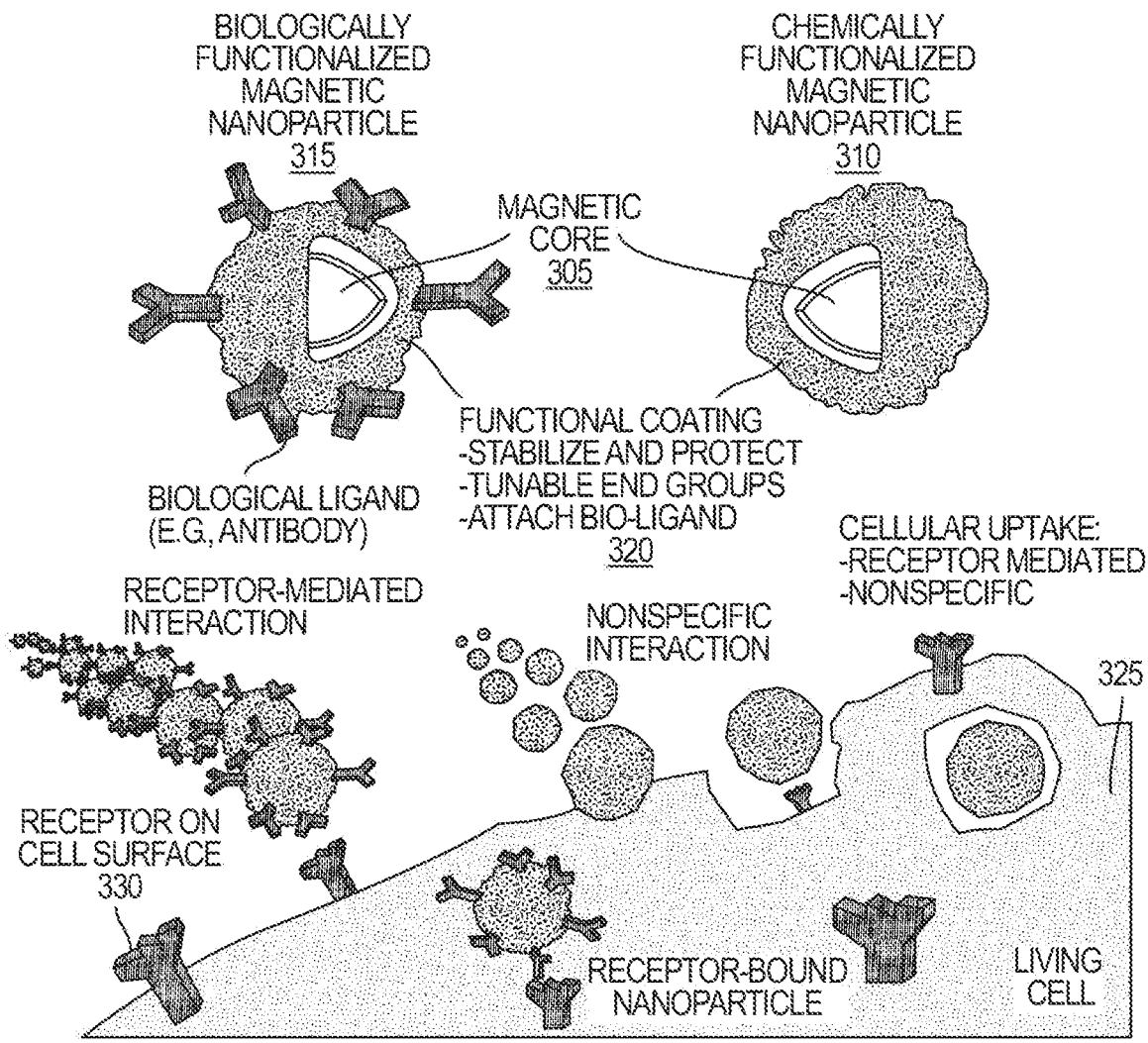
FIG. 3 is an exemplary diagram showing magnetic nanoparticles and their cooperation with an anatomical structure according to an exemplary embodiment of the present disclosure.
Figure 4A:
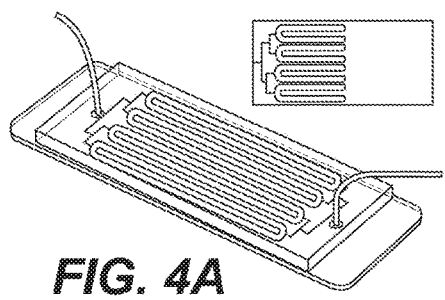
FIGS. 4A-4F are exemplary diagrams illustrating a herringbone-chip and its patterns according to an exemplary embodiment of the present disclosure.
Figure 4B:
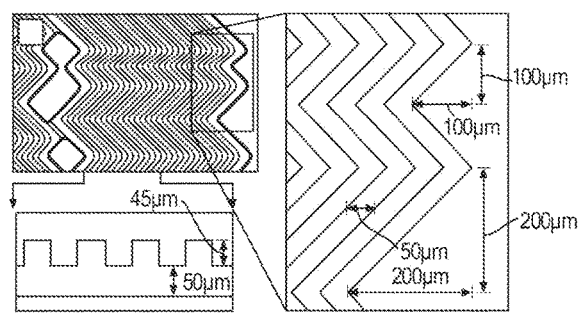
Figure 4C:
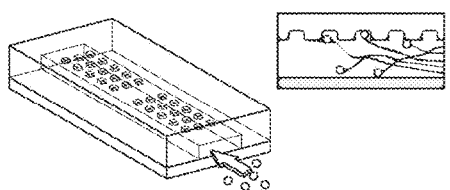
Figure 4E:
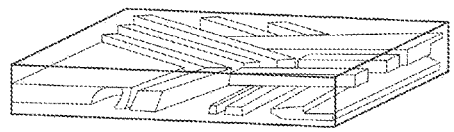
Figure 4D:
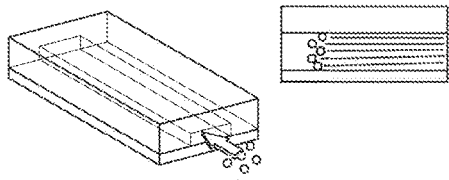
Figure 4F:
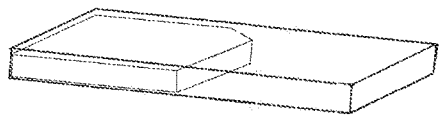

In the exemplary system, the nanoparticles can be made of ferrite and can be coated with cancer killing drugs and adhesion molecules that can bind specifically to cancer cells. (See, e.g., diagram shown FIG. 3). The treatment process can be both chemical and physical. For example, as shown in FIG. 3, the magnetic cores 305 of a chemically functionalized magnetic nanoparticle 310 and biologically functionalized magnetic nanoparticle 315 can include a functional coating 320. Functional coating 320 can be used to stabilize and protect chemically functionalized magnetic nanoparticle 310 and biologically functionalized magnetic nanoparticle 315, as well as being tunable end groups and attached to a bio-ligand. Chemically functionalized magnetic nanoparticle 310 and biologically functionalized magnetic nanoparticle 315 can be used to infiltrate living cell 325 (e.g., at a receptor 330 on the cell surface).

An additional filtration system can be provided which was tested on mice, each of which was injected with half a million murine ovarian cancer cells. The final results showed that mice treated with the exemplary system lived on average one third longer than mice without treatment.

An exemplary experimental group was provided where the fluid from the abdomens of the mice that were injected with cancer cells was removed by researchers, and then the magnetic nanoparticles were added to the fluid and mixed together. A magnetic field was applied that magnetically removed the nanoparticles along with the attached cancer cells.

How the magnetic nanoparticles could be engineered to capture ovarian cancer stem cells, which may not be affected by existing chemotherapy, was also examined. Removing those cells can help eliminate a potent source of new cancer cells. (See, e.g., Reference 6).

Summary of Exemplary Magnetic Nanoparticles
   Speed—It can take time to mix the fluid and nanoparticles together.
   Effectiveness—It proves that the cancer cells can be isolated through magnetic nanoparticles.
   Side effects—When it treats the cell, the cells can be damaged twice more than they are supposed to be damaged.

Exemplary Herringbone-Chip

The circulating tumor cells (e.g., CTCs) that exist in the bloodstream of patients with cancer can provide a potentially accessible source for detection, characterization and monitoring of non-hematological cancers. (See, e.g., diagrams shown FIGS. 4A-4F). For example, FIGS. 4A-4F show exemplary diagrams illustrating a herringbone-chip and its patterns according to an exemplary embodiment of the present disclosure. The CTC-Chip can function by coating microfluidic array of channels with antibodies that can react with epithelial cell adhesion molecule (e.g., EpCAM)-expressing cells which can generally be expressed by most cancer cells.

The exemplary Herringbone ("HB")-Chip design and/or configuration can be different from prior designs of its type in that it can apply passive mixing of blood cells through the generation of microvortices to significantly increase the number of interactions between target CTCs and the antibody-coated chip surface. (See, e.g., Reference 7).

Summary of Exemplary Herringbone-Chip
   Speed—It can take time for cancer cells to attach to the CTC chip.
   Effectiveness—It can work on a small scale and can potentially function on a large scale.
   Side effect—No real side effects since the cancer cells can just attach to the substrate or do nothing.
   Cost—Antibodies and coating material may need to be acquired.
   Easiness of Design—The large chip may have to be extremely detailed.
   Coating the channel can be difficult.

Exemplary Radiation Therapy

Radiation therapy can be a highly targeted and effective way to destroy the tumor cells by using high-energy radiation. X-rays, gamma rays and charged particles can be types of radiation used for cancer treatment. The radiation can be created by a machine outside the body (e.g., external-beam radiation therapy), or it can be produced from radioactive material placed in the body near cancer cells (e.g., internal radiation therapy, also called brachytherapy). Systemic radiation therapy can use radioactive substances, such as radioactive iodine, that travel in the blood to kill cancer cells.

It is believed that approximately half of all cancer patients receive some type of radiation therapy during the course of their treatment. However, radiation therapy can harm DNA when it kills the cancer cells. It can either damage DNA directly, or it can create charged particles within the cells that can in turn damage the DNA. The cells which can be damaged during the processes may eventually stop dividing and/or die. When the damaged cells die, they can be broken down and eliminated by the body's natural processes. Normal cells can be also damaged by radiation therapy which can lead to side effects. Doctors take potential damage to normal cells into account when planning a course of radiation therapy.

Radiation therapy can sometimes be used with curative intent (e.g., that can be, with the hope that the treatment will cure a cancer, either by eliminating a tumor, preventing cancer recurrence, or both). In such cases, radiation can be used with other kinds of therapy or surgery. Radiation therapy can also be given with palliative intent. Palliative treatments may not be intended to cure. Instead, they can relieve symptoms and can reduce the suffering caused by cancer.

Radiation therapy is believed to be the most common way to treat the tumor cells. It can shrink the tumor cells and destroy the tumor cells in the bloodstream. However, it can harm the normal cells, and can negatively affect DNA during the treatment.

Summary of Exemplary Radiation Therapy
   Speed—It can take time to analyze and treat the tumor cells.
   Effectiveness—It can shrink the tumor cells effectively.
   Side effect—When it shrinks the cancer cells, it can damage to normal cells and make DNA changes.
   Cost—The cost can be expensive because the radiation therapy is an advanced technique that is expensive.
   Easiness of design—it is not difficult because the cancer cells can be isolated and detected first with radiation therapy and treated with the exemplary device.

Exemplary Electroporation

Electroporation is a temporary condition of the outer membrane of cells becoming "porous" as a result of high electric fields. While the cells can be porous, normally unwanted fluid and substances can enter into the cell with disturbing effects. This effect can be useful to transfer different material into cells. However, typically about 10,000 to about 100,000 V/cm in a pulse lasting a few microseconds to a millisecond can be utilized for electroporation. The voltage range can vary with different cell size, meaning that the threshold of transmembrane voltage can be different for cells having their own physical property. The determination of the threshold of transmembrane voltage can be beneficial because it can define reversible or irreversible electroporation.

The exemplary advantage of electroporation in the exemplary system, method and computer-accessible medium can be to apply a specific voltage that can be higher than the threshold voltage of certain cancer cells but lower than the threshold voltage of all blood cells in living animals. As is known regarding the electroporation, if voltage can be applied over the threshold voltage, then cell lysis can be induced. Simultaneously, the disadvantage of applying electroporation can be same as the advantage.

Summary of Exemplary Electroporation
   Speed—can be very fast, depending on the flow rate of the device.
   Effectiveness—treatment duration can be very short due to basic cell size property.
   Side effect—can be severe or very little due to voltage applied.
   Cost—machines are readily available.
   Easiness of design—A device can be needed that can facilitate treatment while moving blood laminarly.

Based on the exemplary descriptions above, including accuracy, ease of sterilization, cost, ease to build, and speed, a peristaltic pump can be used for the exemplary design to acquire blood from the patient. The peristaltic pump can be easy to implement in the exemplary device since all that can be needed can be to attach the tubing to the pump. The syringe pump can utilize more modifications to the tubing, and can be overly complicated as well. The exemplary treatment process for the peristaltic pump can also be, for example, twice as fast, which can be beneficial for the exemplary device to treat patients as quickly as possible, without overstressing the blood vessels with high pressure.

The exemplary system, method and computer-accessible medium, according to an exemplary embodiment of the present disclosure, can be used to attenuate CTCs in blood. The exemplary system, method and computer-accessible medium can be suited for tumor cells which have a lower continuous electrical shock threshold than white blood cells and red blood cells, but can be used with multiple shocks as an alternative treatment method for CTCs with higher thresholds. The exemplary system, method and computer-accessible medium, according to an exemplary embodiment of the present disclosure, can draw blood from the testing object in a manner to provide continuous blood flow for use in the electroporation chamber. This can be done by, for example, applying a peristaltic pump and minimum of about 40 inches long tubing to connect the object and the chamber. The tubing size and the flow rate of the exemplary peristaltic pump can be proportional to the size of cuvette. Once the cuvette can be filled, two parallel plates on opposite sides of the electroporation chamber can apply an electric field for a duration long enough to attenuate the CTCs. The peristaltic pump can also facilitate blood to be returned to the object with the same pressure with which it was delivered. A sensor can be provided that can measure the delivered blood pressure as well as one that can monitor the outgoing blood pressure. The treatment can be repeated until about three cycles of whole body blood circulation can be performed.

Exemplary Device/Apparatus Specification

Exemplary Performance

Blood can be extracted by Peristaltic Metering Pump with flow rate of up to 17 ml/s.

Environment

Tubing size: ⅜" (OD)-¼" (ID)

R=⅛"=0.3175 cm

A=0.3165 cm2

V=48.24 ml (e.g., 60" in total tubing)

Testing target: pig—assume 20 kg

Total Volume of Blood approximately 65 ml/kg of body weight

Maximum Volume of Blood draws out approximately 10% of total volume of blood

TVB=1.3 L; MVB=130 ml

Electrode plate

Dimension (mm): 29.5×69.5×2

Stainless Steel 316L

Power Supply setting:

Exemplary voltage: 480 V

Exemplary duration: 100 ms

Distance between two aluminum plate ≤0.8 cm

Electroporated every 4.3 seconds

Approximately 13 ml inside the cuvette

Cuvette dimension (mm):

Distance×width×length

8×25.6×63.6

Figure 5:
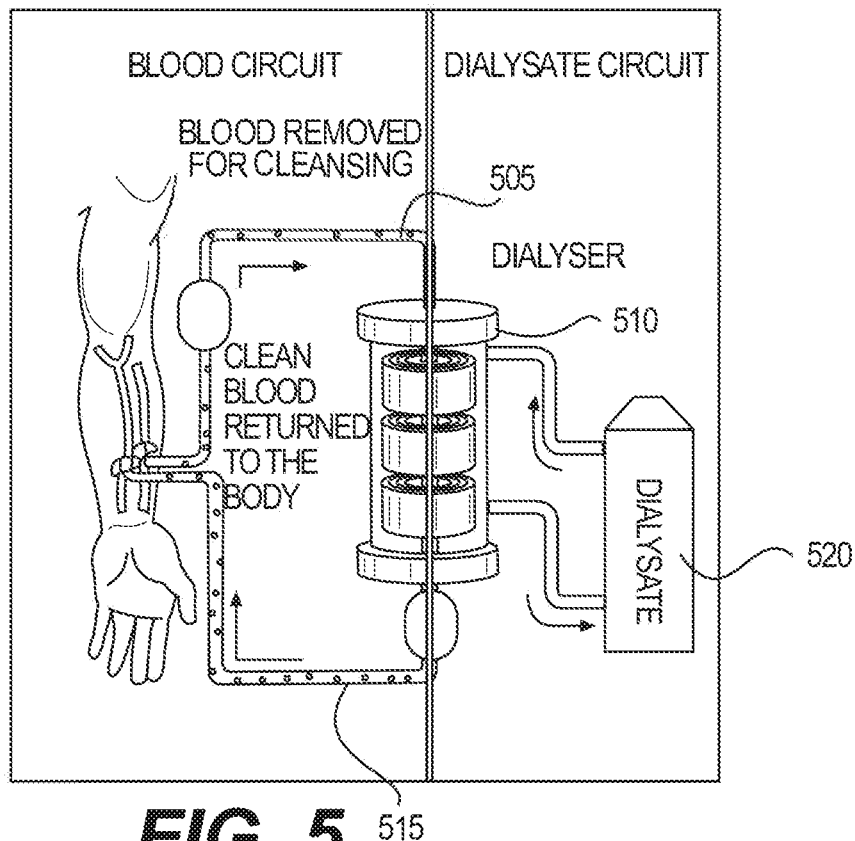
FIG. 5 is an exemplary diagram of a blood circuit of a dialysis system according to an exemplary embodiment of the present disclosure.

Exemplary Dialysis:

Dialysis (e.g., Hemodialysis) is believed to be the most common medical device for treatment for kidney failure, and it can be designed as an artificial kidney in order to remove impurities from patients' blood. (See, e.g., diagram shown FIG. 5). During dialysis, a portion of patient's blood 505 can be removed to circulate through the dialysis machine 510 so the machine can remove impurities, and can control fluid and chemical balances. The purified blood 515 can then be returned to the patient's body. When blood can be circulating externally through the device, the blood can be filtered in the dialyzer 510, which can be made up of two chambers (e.g., one for blood and one for dialysis fluid), which can be separated by a selectively permeable membrane. As blood passes through the dialyzer 510 in the counter direction to the flow of dialysate 520, waste materials and excess water from blood can be drawn through the membrane by diffusion employing a concentration gradient.

The dialysis system can include two or more main parts, for example, the blood and dialysate circuits. Such exemplary circuits can function as pathways for blood and dialysate, respectively. The blood circuit can include several exemplary components.

Exemplary Arterial Pressure Monitor:

This exemplary component can monitor the pressure between the arterial blood access (e.g., a needle) and the blood pump. In order to withdraw the blood out from an artery, the pressure should be negative. Artery alarms can sound in case of patient disconnection, separation of blood tubing or obstruction/kink in the blood circuit.

Exemplary Blood Pump:

The exemplary pump can be a peristaltic pump that can have more than two rollers whose rotation can compress the tubing, thus forcing blood along the tube. The motor rotating the rollers can operate on a low-voltage resulting in a decreased electrical hazard. In addition, the blood pump can be spring-loaded in order to prevent under/over occlusion of the blood tubing (e.g., the pump segment of the tubing can be composed of, or can include, a thicker and/or more resilient material).

Exemplary Heparin Pump:

There is a tendency for blood to clot when it contacts with mechanical devices or synthetic materials. Heparin is the common anticoagulant which prevents blood clotting. Therefore, a syringe pump can be embedded between the blood pump and the dialyzer to prevent blood embolism.

Exemplary Air Leak Detector:

Air in bloodstream is a medical emergency which causes air embolism. Thus the air detector can check if air gets into patient's bloodstream and can shut off the device in case of air leakage.

Exemplary Venous Pressure Monitor:

This exemplary component can monitor the pressure between the venous drip chamber and the venous needle. Out-of-range pressures can trigger clamping of the blood line, stopping of the blood pump, and activation of appropriate alarms, shutting the venous return.

Blood Tubing:

Blood tubing can be made of biocompatible and nontoxic materials. The blood tubing in the exemplary pump segment can be treated with silicone to minimize blood clotting. (See, e.g., Reference 14).

Figure 6:
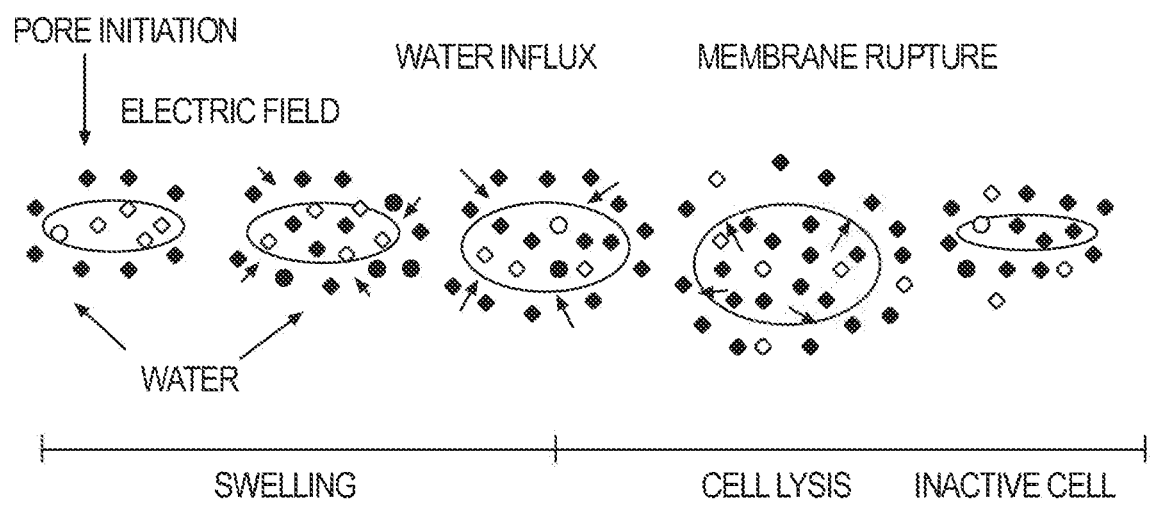
FIG. 6 is an exemplary diagram illustrating the electroporation of a cell membrane according to an exemplary embodiment of the present disclosure.

Exemplary Electroporation:

Electroporation (see, e.g., diagram shown FIG. 6) is a technique that uses micro to milliseconds electric pulses to create pores in the cell membrane, facilitating molecules that are normally incapable of crossing the cell membrane to enter the cell. (See, e.g., References 8 and 10). Electroporation applications cover many fields including gene insertion in cells also known as electrogene therapy, and for the treatment of cancer also known as electrochemotherapy. In electrochemotherapy, the opening of pores in the cell membrane can facilitate the molecules or other chemotherapeutic agent to enter the cell at greater, more effective concentration and exert its cytotoxic action killing the target cell. (See, e.g., Reference 9). FIG. 6 shows an exemplary diagram illustrating the electroporation of a cell membrane according to an exemplary embodiment of the present disclosure. In order to perform pore initiation, an electric field is applied to the cell. After the electric field is applied, water from outside of the cell can enter into the cell, swelling the cell. The cell then ruptures due to the influx of the water, and then becomes an inactive cell.

However, if the applied electric field can be higher than a certain threshold, cells are unable to seal the pores itself, therefore, causing cell death due to the loss of homeostatic mechanisms. This phenomenon can be called irreversible electroporation ("IRE"). (See, e.g., Reference 11). For different types of cell or tissue, the threshold electric field can be varied. A general trend can be found in the use of electroporation to introduce molecules into cells. For a given pulse shape, small magnitude pulses can have no effect, but at about 1 kV/cm for mammalian cells and short pulses, some cells can experience molecular uptake. As larger electric fields are used, the percentage of participating cells can increase, but the percentage of surviving cells can simultaneously decrease. (See, e.g., References 12 and 13). No cells can survive under a very large electric field because a prompt membrane rupture can occur in some portions of the cell membrane, leading to a large hole in the membrane. An exemplary advantage of irreversible electroporation over electrochemotherapy can be the avoidance of drugs, as it only relies on the electric field to kill the cancer cells.

Several known devices utilize an electroporation procedure in order to treat tumor cells in the target tissue also called Electroporation-based therapies ("EBTs"). An effective electroporation procedure for EBTs is a procedure which makes it possible to spare major blood vessels, extracellular matrix and other sensitive or critical structures in the treatment process as opposed to thermal ablation. The procedure can include the delivery of low-energy electric pulses through minimally invasive electrodes inserted within the tissue. The target tissue can be exposed to external electric field distributions around the electrodes, which can alter the resting transmembrane potential of the cells. The degree of tissue electroporation can depend on the magnitude of the induced transmembrane potential.

An exemplary IRE device can be the NanoKnife® in which a small electric pulse generator can be used to set the desired IRE pulse parameters (e.g., voltage, pulse duration, number of pulses and pulse frequency). This exemplary device can include two electrodes that can be configured to be inserted into the tumor tissue. The two sets of pulse strengths can be delivered in perpendicular directions to ensure uniform coverage of the tumor and can be synchronized with the electrocardiogram ("ECG") signal to prevent ventricular fibrillation or cardiac arrhythmias.

When the electric potential can be applied to the electrodes, electric force can drive ions towards one electrode or the other. This can also lead to undesirable behavior such as electrolysis, separating water into its hydrogen and oxygen components, and can lead to the formation of bubbles at the electrode-tissue interface. These effects can be further exacerbated in multiple pulse applications. In addition, such effects can cause interference with treatment by skewing electric field distributions, and altering treatment outcomes in a relatively unpredictable manner. Therefore, the sets of pulses can be delivered with alternating polarity between the sets, in order to significantly reduce these side effects.

The concept of treating blood externally using electricity in a flow apparatus has been previously described in U.S. Pat. No. 5,139,684, the entire the entire disclosure of which is incorporated herein by reference. It is known that blood from donors can sometimes be contaminated with bacteria, viruses, fungus or parasites. Blood from blood banks can then be contaminated from even a single donor. The whole batch must then be discarded for transfusion purposes. The process and system was developed using an electric field to attenuate blood or other fluids from donors or patients. This electric field was applied directly on the tubing that connected to the patient via a modified conductive vessel. Since only the needle can be electrically isolated from the patient, only a small about 0.2 to about 12V voltage can be used to create a one microampere per square millimeter current flow Exemplary Microfluidic Device:

Although CTCs can provide a connection between the primary tumor and metastatic sites, the factors involved in circulating tumor cell survival in the blood circulation may not be fully understood. However, the CTCs in blood stream are extremely rare events, approximately 1 to 10 for each milliliter of whole blood which contains millions of white blood cells and billions of red blood cells. A small number of CTCs can indicate that to capture these cancer cells from whole blood can be difficult. However, previous research has found that microfluidic device can be used to detect CTCs in blood.

Figure 7:
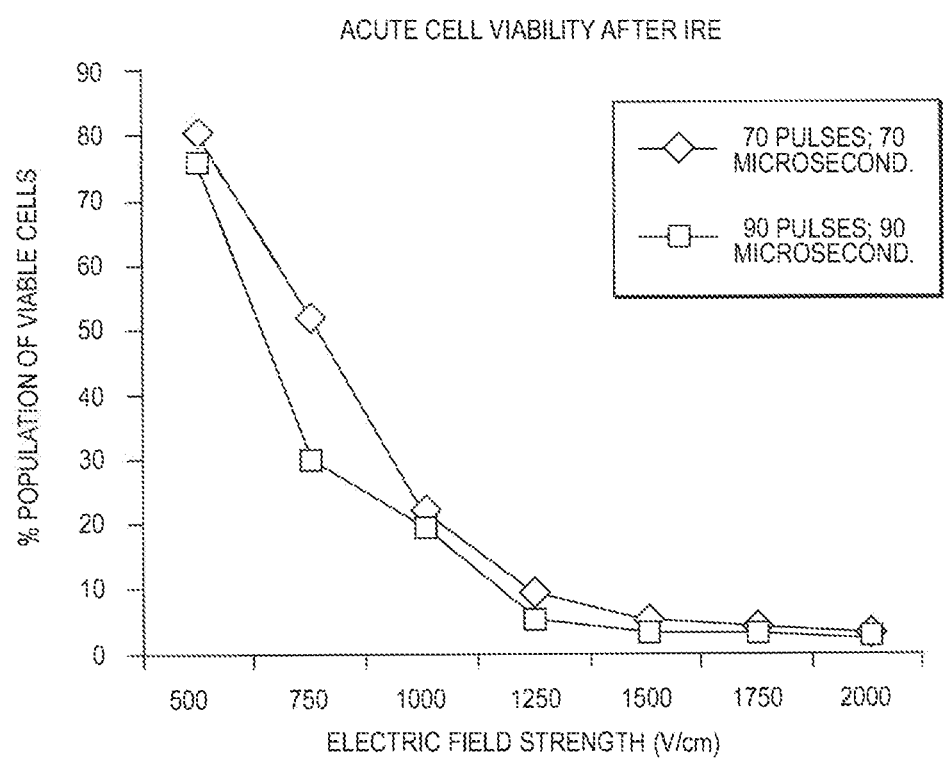
FIG. 7 is an exemplary graph illustrating cell viability based on differing electric field strengths according to an exemplary embodiment of the present disclosure.

FIG. 7 shows an exemplary graph illustrating cell viability based on differing electric field strengths according to an exemplary embodiment of the present disclosure.

Microfluidic devices have already proved that exposure to an electric field with a different time line can selectively remove circulating tumor cell without harming healthy blood cells. IRE is a mechanism that can target circulating tumor cells at the cellular level with short electrical pulses. IRE can break open the cancer cell membrane, losing homeostatic balance, which can cause the cancer cells to die. The study showed that the threshold for red blood cells was about 1100 V/cm while for cancer cells it was about 600 V/cm. White blood cells died regardless of the application of voltage or not. Thus, at about 600 V/cm, electroporation is a viable way to treat whole blood as it only kills the cancer cells while doing minimal harm to red and white blood cells. Although cancer cells, (e.g., erythrocyte and leukocyte) were treated separately in buffer solution with extremely little volume in this research, the data shows that the voltage applied and the exposure time to electric field are electroporation used parameters to determine cells viability. (See, e.g., Reference 16).

Exemplary Device/Apparatus

Figure 8:
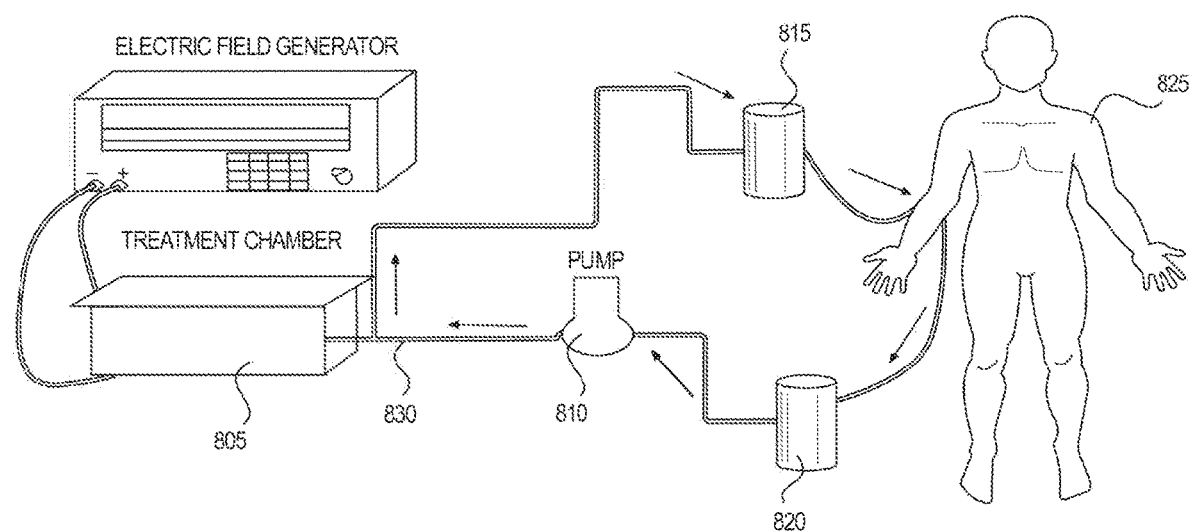
FIG. 8 is an exemplary schematic diagram of the exemplary system according to an exemplary embodiment of the present disclosure.

The exemplary device, according to an exemplary embodiment of the present disclosure, can include certain exemplary parts, for example, an electroporation (e.g., treatment) chamber 805 and a peristaltic pump 810, and two sub (e.g., connecting) parts 815 and 820, tubings and luer locks. (See, e.g., schematic shown in FIG. 8). When blood can be withdrawn from a patient body 825, such blood flow can be continuously driven by a peristaltic pump 810 into an electroporation chamber 805 through tubings 830. After blood can be treated with an electroporation system in the chamber 805, the pump 810 can drive the flow to infuse the treated blood into the patient 825. To ensure the connection of tubings, luer locks can be used.

Exemplary Pump

The exemplary peristaltic pump used with the exemplary embodiment of the present disclosure can be the MityFlex 913 (as one example) with an exemplary ¼" tubing size, and can provide an adjustable and high enough flow rate (e.g., so that a higher flow rate can be used). The pump can provide the pressure needed to move the blood in the tubing. It should be understood that other exemplary pumps and tubing, as well as other components, can be used according to an exemplary embodiment of the present disclosure.

Exemplary Chamber

Figure 9:
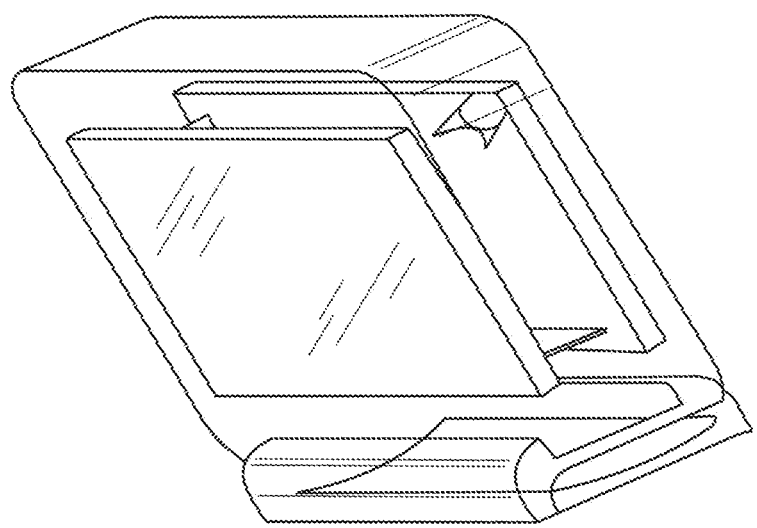
FIG. 9 is an exemplary diagram of an exemplary treatment chamber according to an exemplary embodiment of the present disclosure.

As shown in the diagram of FIG. 9, the exemplary design of the exemplary electroporation chamber can be based on the fact that CTCs can be killed in the chamber. The exemplary dimensions of the exemplary chamber can be as follows, but not limited thereby:

|  | Length(cm) | Height(cm) | Width(cm) | Volume(ml) |
|---|---|---|---|---|
| Outside | 8.40 | 4.56 | 1.20 | 45.96 |
| Inside/Opening | 6.36 | 2.56 | 0.80 | 13.03 |
| Plate/Groove | 7.12 | 3.04 | 0.20 | 43.29 |

**Diameter of Inlet and Outlet: 0.2 cm

The exemplary chamber can be rectangular, and can hold up to about 13.03 ml of blood within this chamber size. The chamber can have openings whose length and height can be the same as the dimension of inside chamber, and grooves whose dimensions can be the same as the electrode's dimension on the sides. The openings can also be covered by the electrodes (e.g., plates), which can be inserted into the grooves. The inside chamber width can be the same as the plate separation distance (e.g., 0.8 cm), and this can be based on the maximum voltage of the exemplary electroporation system, which can be about 500V, and on the exemplary desired electric field which can be about 600 V/cm. Therefore, about 0.8 cm can be the maximum separation distance needed to obtain the desired electric field.

Exemplary Tubings

The tubing for the exemplary device can be made up of ultra-clear S-50-HL Tygon PVC, a biocompatible material, which can function as a path of blood circulation. The tubing can provide a pathway to blood flow between the withdrawal needle and the pump, the pump and the chamber, and then chamber and the infusion needle. Its inner diameter, outer diameter, and wall thickness can be about ¼, about ⅜, and about 1/16 inches, respectively. The dimension can be based on a suitable exemplary size to prevent blood coagulation, and to match the size of the luers.

Exemplary Luers

The luers can facilitate connecting tubing to tubing, tubing to needle, and tubing to chamber. The tubing alone may not be rigid, and there can be leakage if it is not connected using another part. The luers can ensure, or otherwise facilitate, the exemplary connections can be tight and leak free. They can also provide a simple mechanism to assemble, disassemble and replace the various components of the exemplary system. The exemplary luer size used can be one that matches the ¼" diameter of the exemplary tubing.

Exemplary Tests

Exemplary Fluid Leaking Test

Figure 10:
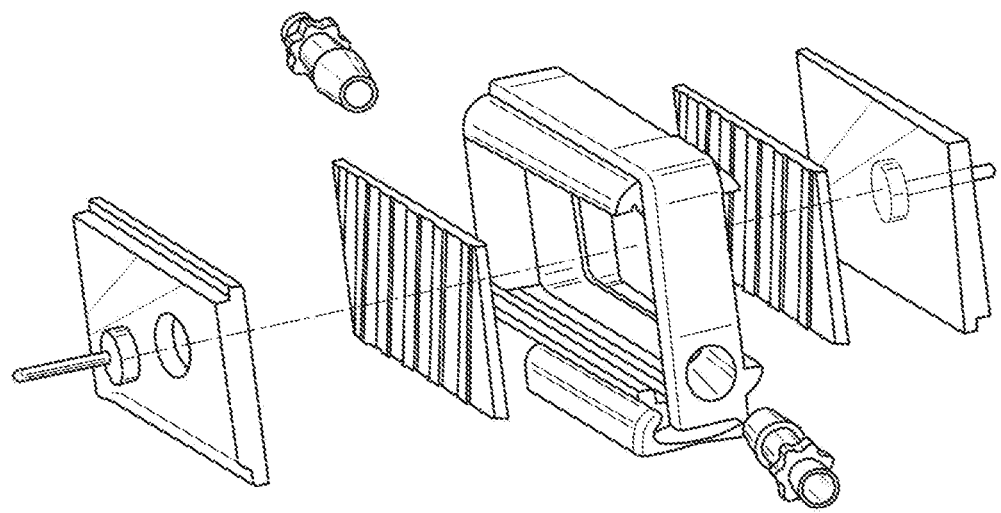
FIG. 10 is an exemplary diagram of the exemplary treatment chamber of FIG. 9 having various exemplary components attached thereto, or provided therein, according to an exemplary embodiment of the present disclosure.

A concern about the exemplary device can be how to prevent fluid leakage. To this end, stainless steel plates can be glued to the chamber with cyanoacrylate glue so that the plates can function as both electrodes that carry voltage within the chamber and as covers of the chamber. The cover plates can be slid and glued onto the stainless steels plates with silicone glue so that the cover plates can function as a secondary method to prevent fluid leakage from the chamber. Similar to such glues and plates, luer locks can be used to establish a tight connection of tubing to tubing. To ensure the quality of the connections (e.g., there should be no leakage), the exemplary system for transferring about 600 ml of water can be run at a maximum flow rate, which can induce the maximum pressure in the system that the pump can provide to ensure that there is no water leaking out of the connections. With these exemplary methods, it was experimentally proven that there is no leakage from the exemplary device. (See, e.g., diagram shown in FIG. 10). In particular, FIG. 10 shows an exemplary diagram of the exemplary treatment chamber of FIG. 9 having various exemplary components attached thereto, or provided therein, according to an exemplary embodiment of the present disclosure.

Exemplary Flow Rate Test

Figure 11:
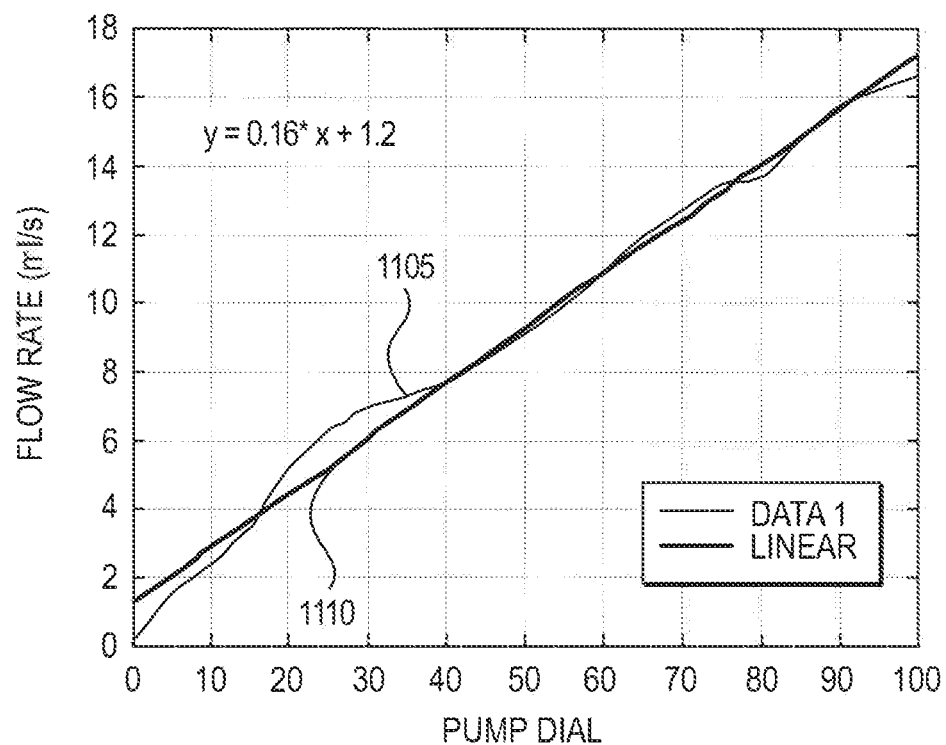
FIG. 11 is an exemplary graph illustrating the flow rate corresponding to each exemplary pump dial setting according to an exemplary embodiment of the present disclosure.

Previously, the flow rate of the peristaltic pump was tested without the chamber in order to determine what flow rate the numbers around the dial of the pump represents. However, since the exemplary system/apparatus can include the chamber, the exemplary flow rate test was redone using the chamber as was the Fluid Leaking Test. After filling up the tubing circuit and chamber, two reservoirs were set up; one filled with about 600 ml and the other being empty. The inlet was placed in the about 600 ml reservoir, and the outlet was placed in the empty reservoir. The peristaltic pump was run at different dials and timed as to how long it took for a specific amount of volume to transfer to the empty reservoir (e.g., approximately 400 ml of transfer volume for each test was used). FIG. 11 shows a graph that illustrates a plot of the flow rate obtained at each dial setting. From this exemplary testing, it can be determined that the maximum flow rate that can be achieved from the exemplary device can be about 16.5 ml per second based on the data 1 line (e.g., element 1105) and the linear line (e.g., element 1110). (See, e.g., graph shown in FIG. 11).

Exemplary Current Leakage Test

The current flowing through the tubing, and into the patient, can be examined. For safety reasons, a small and safe voltage source was used to test for current leakage. A 9V battery was used as the exemplary power source, and it was connected it to the exemplary plates. The system was run, and the current was measured across the inlet and outlet reservoirs. The current was found to be zero. It was later tested with the power supply on about a 480V setting, and the full on output on current and power. While the power supply was unable to achieve the about 480V setting, it provided a voltage which was around 5V. The current associated with this voltage across the reservoir was about 0.000 mA. The exemplary current can be less than 10 mA for high voltage.

Exemplary Plate-Connector Contact Validation Test

The exemplary banana jacks were verified with the stainless steel plates by using a multimeter to measure the resistance across the empty chamber. The resistance was found to be about 6 MΩ which can be about the resistance of air as expected. The chamber was then filled with water and the resistance was measured across the chamber again. The resistance was found to be about 2.6 MΩ, which can be about the resistance of water, as expected. This confirmed that the banana jacks made contact with the plates because the resistance would stay the same if they were not making contact. The resistance was also tested with saline running through the system, and the resistance was found to be about 1.7 MΩ. However, this resistance appeared to rise over time.

Exemplary Treatment Time Threshold Test

Figure 12:
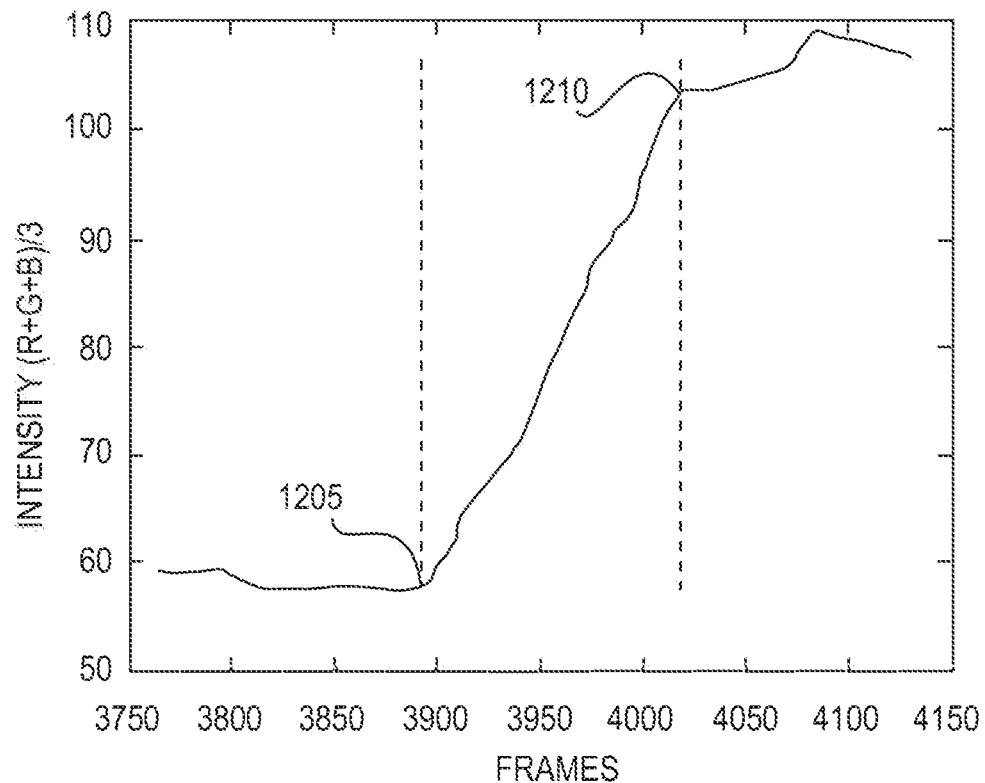
FIG. 12 is an exemplary graph illustrating the respective value for each frame of video according to an exemplary embodiment of the present disclosure.

As the pump can push the new fluid into the system, and old fluid can be flowing out of or otherwise provided by the system at the exemplary desired flow rate, there can be no way to tell when all of the old fluid leaves the system. While the old volume can be pushed out, a portion can be left behind and mixed with the new fluid. To address this issue, the circuit and chamber were filled with dye. This dye within the chamber represented the "old fluid" of the system. The inlet was placed in a reservoir of clear water which represented the "new fluid". As the new fluid moved into the chamber, the color of the chamber changed. A video of the change in color was taken and Image J was used to analyze the change in color intensity per frame. FIG. 12 shows a graph of the RGB average for each frame in the video.

Figure 13:
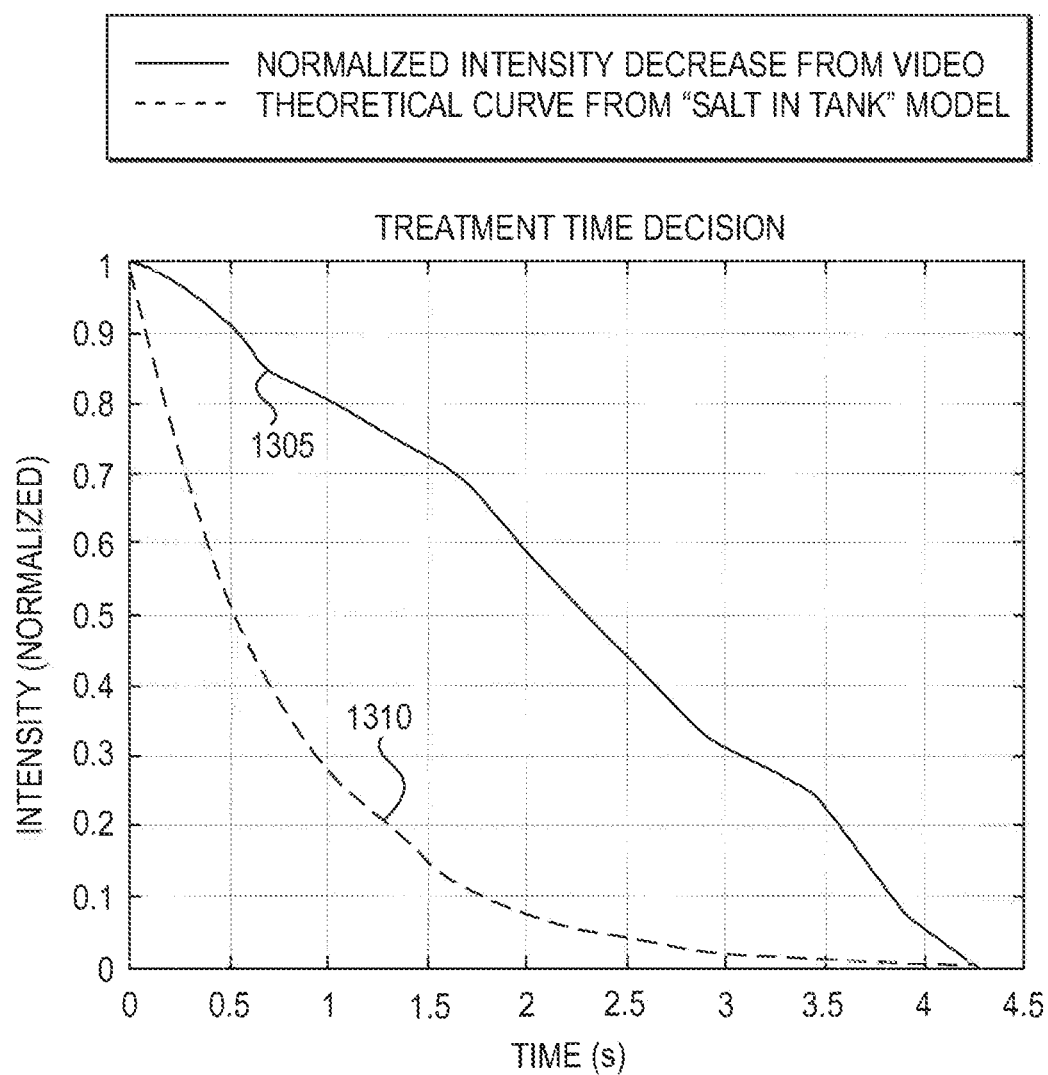
FIG. 13 is an exemplary graph illustrating the normalized intensity of the dye over time according to an exemplary embodiment of the present disclosure.

As shown in the graph of FIG. 12, the points at which new fluid started entering the chamber (e.g., element 1205) can be seen as well as when the chamber was essentially filled with new fluid (e.g., element 1210). It was concluded that the time for 100% of the old fluid to clear the chamber was about 4.3 second. This was also mathematically verified by setting up a "salt in a tank" model and using 5*τ (5 time constants tau to achieve less than about 1% left) as the exemplary "100% clearance", found that value to be about 3.8 seconds. (See, e.g., graph shown in FIG. 13). For example, the graph shown in FIG. 13 illustrates a comparison of the time versus the normalized intensity for the normalized intensity decrease from video 1305 and the theoretical curve from the exemplary "salt in tank" model 1310.

Exemplary Power Supply Calibration Test

Figure 14:
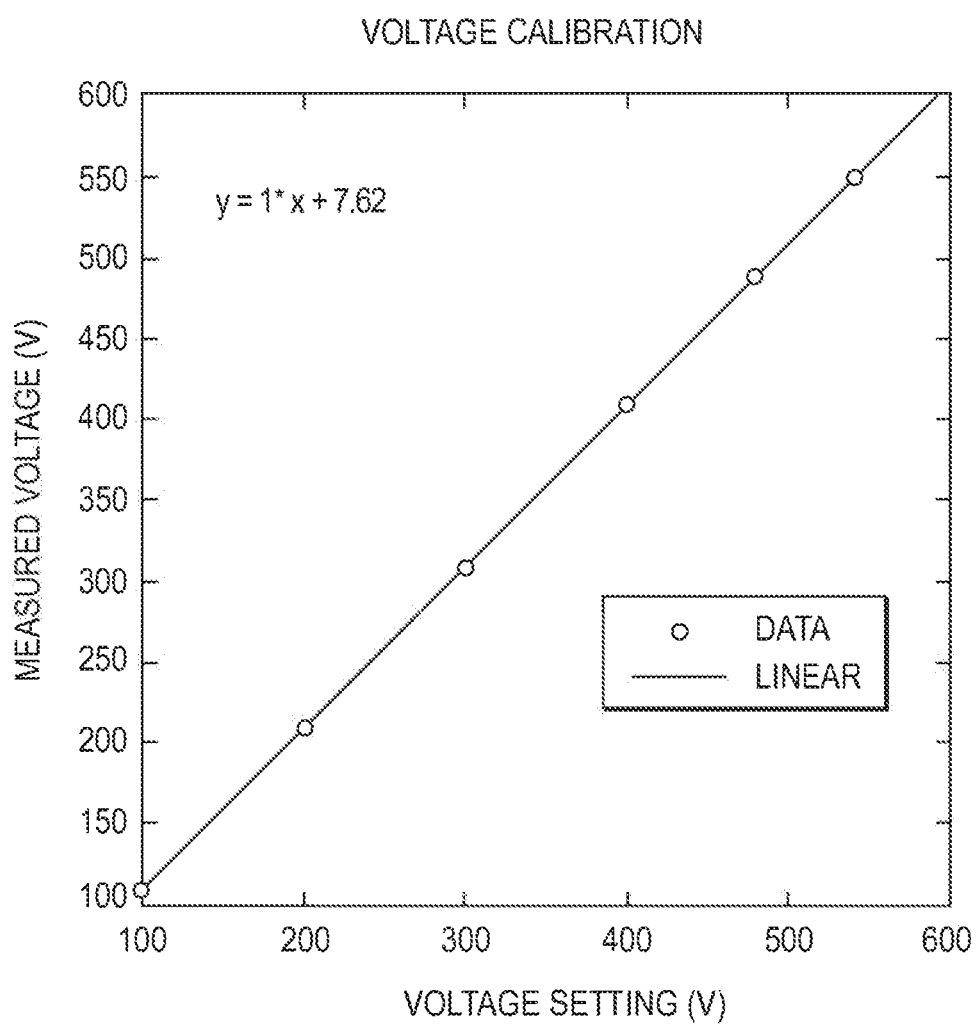
FIG. 14 is an exemplary graph illustrating the voltage setting versus measured voltage for an exemplary power supply according to an exemplary embodiment of the present disclosure.
Figure 15:
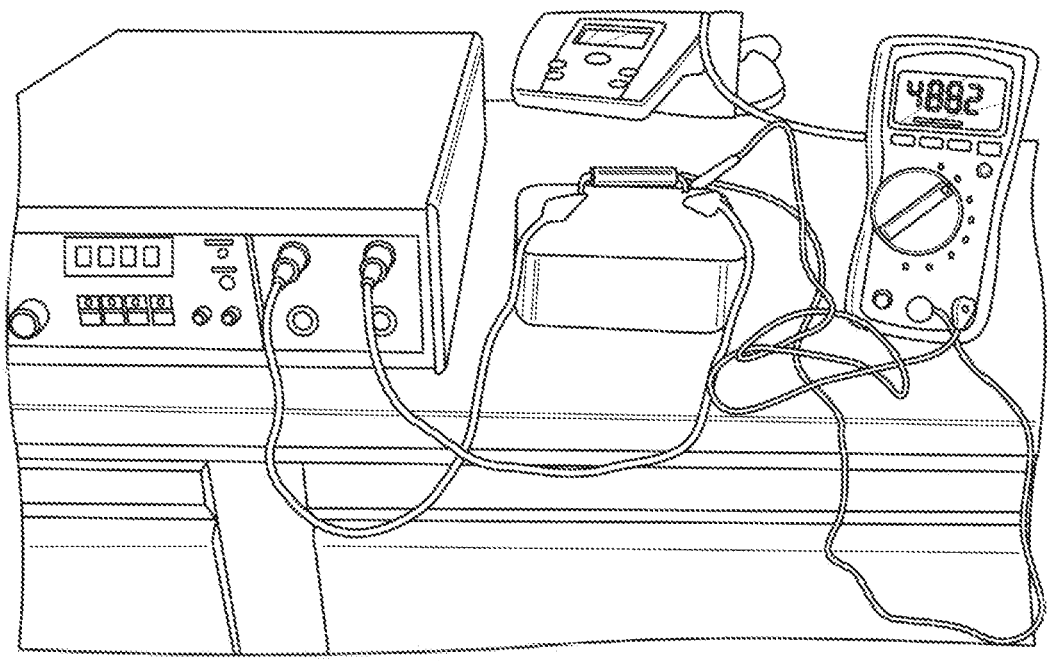
FIG. 15 is an exemplary photograph of an exemplary power supply according to an exemplary embodiment of the present disclosure.

The Pharmacia LKB-ECPS 3000/150 electrophoresis power supply can be used as the exemplary power generator. Because a power supply can be used, a verification was made as to whether the power supply was outputting the voltage seen on the LED. The power supply which provided constant electric field was measured at certain voltage with multimeter. There can be a little difference between multimeter and the device (e.g., about 7.2V higher), but it can be acceptable since the power supply can be designed for high voltage output and the settings can be adjusted in increments of ten. (See, e.g., graph shown in FIG. 14 and image shown in FIG. 15).

Figure 16:
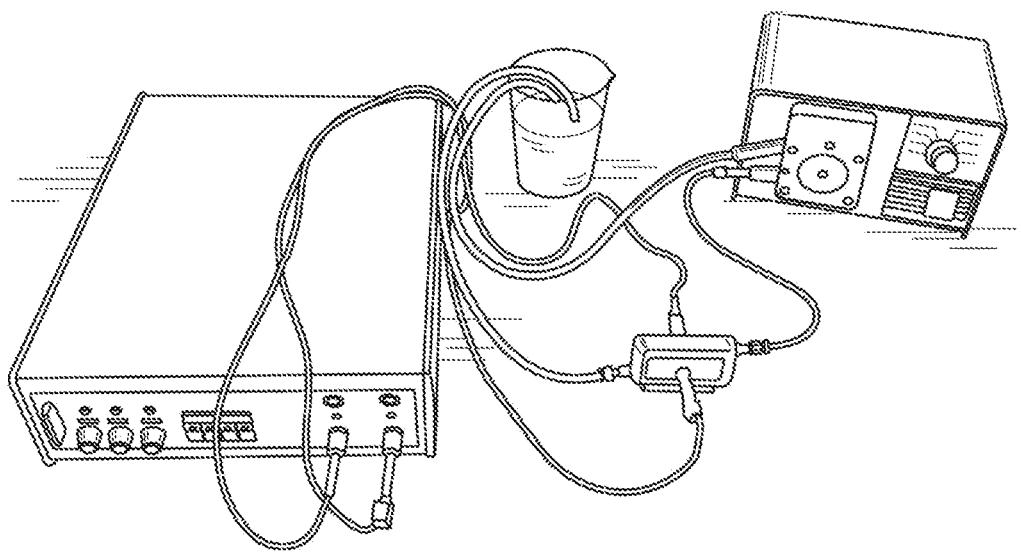
FIG. 16 is an exemplary photograph of the exemplary system according to an exemplary embodiment of the present disclosure.

FIG. 16 shows an exemplary image of the exemplary system/apparatus according to an exemplary embodiment of the present disclosure.

Figure 17:
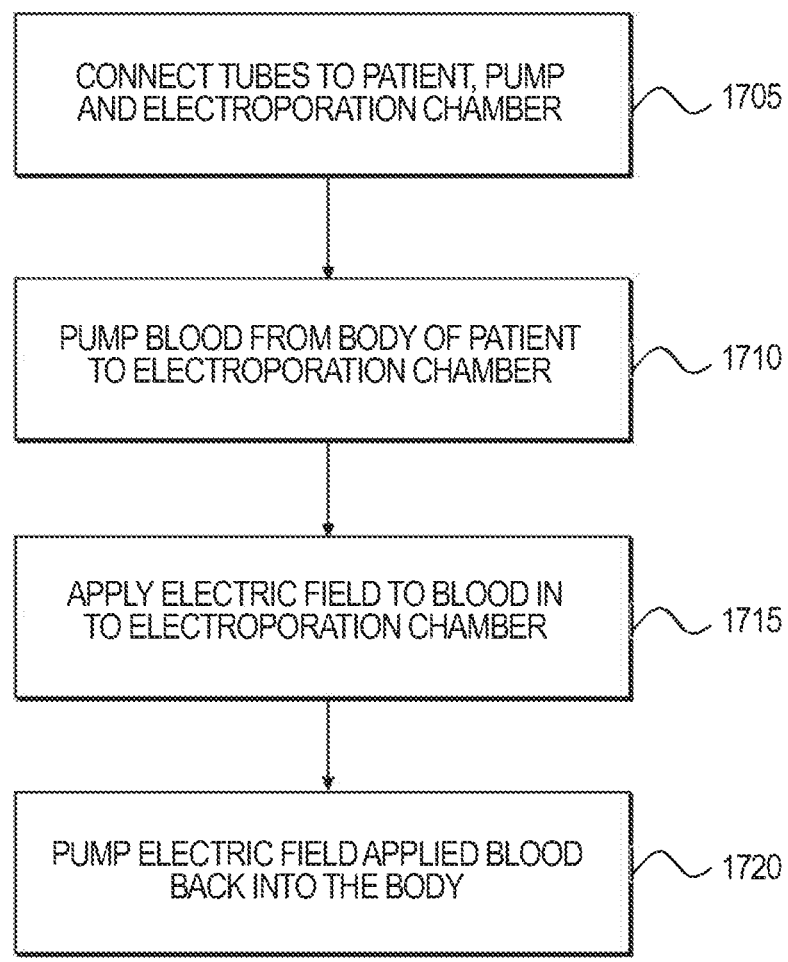
FIG. 17 is an exemplary flow diagram of an exemplary method for killing circulating tumor cells according to an exemplary embodiment of the present disclosure.

FIG. 17 shows an exemplary flow diagram of an exemplary method 1700 for killing circulating tumor cells according to an exemplary embodiment of the present disclosure. For example, at procedure 1705, tubes can be connected to the patient, a pump and an electroporation chamber. At or 1710, blood from the body of the patient can be pumped into the electroporation chamber. At procedure 1715, an electric field can be applied to the blood located in the electroporation chamber. At procedure 1720, the electric field applied blood can be pumped back into the body.

Figure 18:
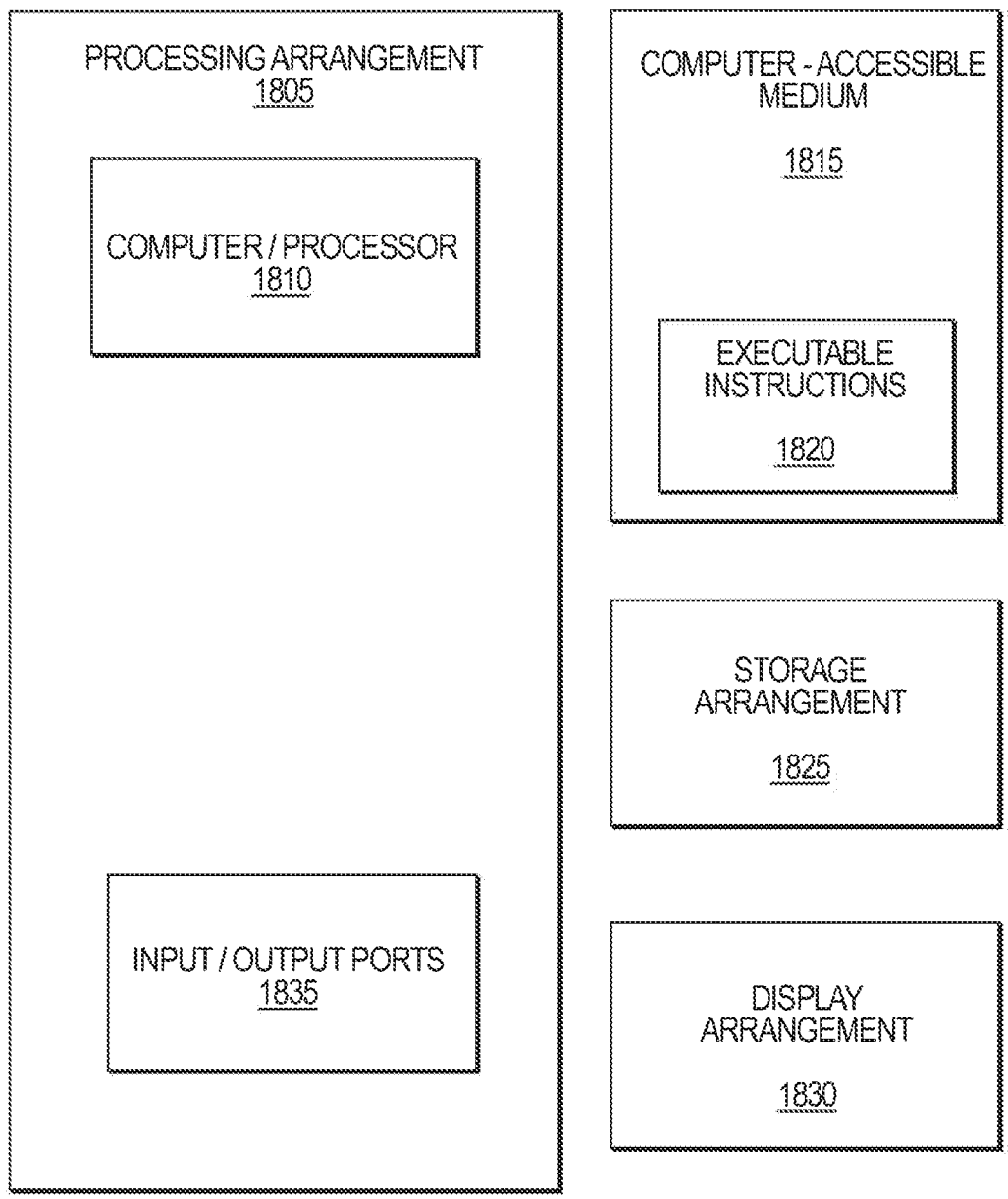
FIG. 18 is an illustration of an exemplary block diagram of an exemplary system in accordance with certain exemplary embodiments of the present disclosure.

FIG. 18 shows a block diagram of an exemplary embodiment of a system according to the present disclosure. For example, exemplary procedures in accordance with the present disclosure described herein can be performed by a processing arrangement and/or a computing arrangement 1802. Such processing/computing arrangement 1802 can be, for example entirely or a part of, or include, but not limited to, a computer/processor 1804 that can include, for example one or more microprocessors, and use instructions stored on a computer-accessible medium (e.g., e.g., RAM, ROM, hard drive, or other storage device).

As shown in FIG. 18, for example a computer-accessible medium 1806 (e.g., e.g., as described herein above, a storage device such as a hard disk, floppy disk, memory stick, CD-ROM, RAM, ROM, etc., or a collection thereof) can be provided (e.g., e.g., in communication with the processing arrangement 1802). The computer-accessible medium 1806 can contain executable instructions 1808 thereon. In addition or alternatively, a storage arrangement 1810 can be provided separately from the computer-accessible medium 1806, which can provide the instructions to the processing arrangement 1802 so as to configure the processing arrangement to execute certain exemplary procedures, processes and methods, as described herein above, for example.

Further, the exemplary processing arrangement 1802 can be provided with or include an input/output arrangement 1814, which can include, for example a wired network, a wireless network, the internet, an intranet, a data collection probe, a sensor, etc. As shown in FIG. 18, the exemplary processing arrangement 1802 can be in communication with an exemplary display arrangement 1812, which, according to certain exemplary embodiments of the present disclosure, can be a touch-screen configured for inputting information to the processing arrangement in addition to outputting information from the processing arrangement, for example. Further, the exemplary display 1812 and/or a storage arrangement 1810 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
1. National Cancer Institute, http://www.cancer.gov, accessed Dec. 9, 2011
2. Ali D., Le Scodon R., Treatment of the primary tumor in breast cancer patients with synchronous metastases, annals of oncology, 2010
3. Harvard Apparatus, http://www.harvardapparatus.com, accessed Nov. 14, 2011
4. Pumps & Systems, http://www.pump-zone.com, accessed Nov. 14, 2011
5. First Ten Angstroms, http://www.firsttenangstroms.com, accessed Nov. 14, 2011
6. Jurgons, R. et al. Drug loaded magnetic nanoparticles for cancer therapy. Journal of Physics: Condensed Matter. September 2006; 18:S2893
7. Wang S. et al. Highly efficient capture of circulating tumor cells by using nanostructured silicon substrates with integrated chaotic micromixers, doi: 10.1002.
8. Bao, N. et al. A microfluidic electroporation device for cell lysis, April 2004, doi: 10.1039

9. Lu C. et al. Microfluidic electroporation of tumor and blood cells: observation of nucleus expansion and implications on selective analysis and purging of circulating tumor cells, January 2010.
10. Fox, M. B. et al. Electroporation of cells in microfluidic devices: a review, Anal Bioanal Chem, 385: 474-485, 2006
11. Walters, R. E., King, A. D., United States patent application Publication: Large volume ex vivo electroporation method, Pub. No.: US2006/0108229, Pub. date: May 25, 2006
12. Weaver J. C., Electroporation: A general phenomenon for manipulating cells and tissues, Harvard-MIT division of health sciences and technology, Massachusetts Institute of Technology.
13. Bertacchini, C. et al, design of an irreversible electroporation system for clinical use, volume 6, page 313-320, August 2007.
14. Pump System Inc. http://www.syringepump.com/index.php, accessed Dec. 9, 2011
15. University of Maryland Medical Center, http://www.umm.edu/patiented/articles/what_radiation_therapies_non-small_cell_lung_cancer_000072_11.htm
16. SolidState Technology, http://www.electroiq.com/articles/stm/2008/02/bbiomedical-applications-using-magnetic-nanoparticles-b.html
17. Stott S, Hsu C, Toner M, et al. Isolation of circulating tumor cells using a microvortex-generating herringbone-chip. Proceedings Of The National Academy Of Sciences Of The United States Of America. Oct. 26, 2010; 107 (e.g., 43):18392-18397
18. Misra M. The basics of hemodialysis equipment. Hemodialysis International. January 2005; 9 (e.g., 1):30-36.
19. Kinetics of Microbial Inactivation for Alternative Food Processing Technologies—Pulsed Electric Fields, http://www.fda.gov/food/scienceresearch/researchareas/safe-practicesforfoodproc esses/ucm101662.htm
20. VII. Bao, N. et al. A microfluidic electroporation device for cell lysis, April 2004, doi:
21. U.S. Pat. No. 3,737,251
22. U.S. Pat. No. 5,705,018
23. U.S. Pat. No. 5,139,684

What is claimed is:

1. An apparatus, comprising:
a circulating tumor cell (CTC) treatment arrangement;
a pump arrangement configured to (i) circulate a fluid through the CTC treatment arrangement; and
an electric field generator electrically connected to the CTC treatment arrangement, and configured to apply an electric field to the fluid circulating through the CTC treatment arrangement,
wherein the pump arrangement is further configured to pump the electric field applied fluid to a body of a patient, and
wherein the CTC treatment arrangement includes tubing, and wherein the electric field generator is configured to directly apply the electric field on the tubing to the fluid circulating through the CTC treatment arrangement.

2. The apparatus of claim 1, wherein the pump arrangement is at least one of (i) a peristaltic pump, or (ii) configured to continuously circulate the fluid through the CTC treatment arrangement.

3. The apparatus of claim 1, wherein the fluid is blood from the patient.

4. The apparatus of claim 1, wherein the electric field at least one of (i) is configured to kill at least one CTC in the fluid, or (ii) includes a plurality of micro pulses.

5. The apparatus of claim 1, wherein the CTC treatment arrangement includes at least one of (i) at least one electroporation chamber, or (ii) an input port and an output port.

6. The apparatus of claim 5, further comprising a plurality of electrodes positioned inside of the electroporation chamber electrically connected to the electric field generator.

7. The apparatus of claim 5, further comprising:
a first tube connected to the output port and configured to be inserted into the body of the patient;
a second tube configured to be inserted into the body and connected to the pump arrangement; and
a third tube connected to the pump arrangement and the input port of the CTC treatment arrangement,
wherein the pump arrangement is configured to pump the electric field applied fluid to the body via the first tube.

8. A method for killing at least one circulating tumor cell (CTC), comprising:
pumping blood from a body of a patient to an electroporation chamber inside of a CTC treatment arrangement to circulate the blood;
applying an electric field to the circulating blood located in the electroporation chamber in order to kill the at least one CTC; and
pumping, using a pump arrangement, the electric-field-applied-circulating blood back into the body,
wherein the electric field is directly applied to the blood on tubing located in the CTC treatment arrangement in order to kill the at least one CTC.

9. The method of claim 8, wherein the pumping of the blood from the body is performed using the pump arrangement.

10. The method of claim 9, wherein the pump arrangement includes a peristaltic pump.

11. The method of claim 9, further comprising:
pumping further blood from the body to the electroporation chamber;
applying a further electric field to the further blood located in the electroporation chamber in order to kill at least one further CTC; and
pumping the further electric field-applied blood back into the body using the pump arrangement.

12. The method of claim 9, wherein the electric field includes a plurality of micro pulses.

13. The method of claim 9, wherein the electroporation chamber includes at least one of (i) a plurality of electrodes electrically connected to a field generator, or (ii) an input port and an output port.

14. The method of claim 13, further comprising:
connecting a first tube to the output port of the electroporation chamber;
connecting a second tube to the pump arrangement; and
connecting a third tube to the pump arrangement and the input port,
wherein the pumping of the electric field applied blood to the body is performed via the first tube.

15. The method of claim 14, further comprising inserting the first tube and the second tube into the body.

16. A non-transitory computer-accessible medium having stored thereon computer-executable instructions for killing at least one circulating tumor cell (CTC), wherein, when a computer arrangement executes the instructions, the computer arrangement is configured to perform procedures comprising:

controlling pumping blood from a body of a patient to an electroporation chamber inside of a CTC treatment arrangement to circulate the blood;

controlling an application of an electric field to the circulating blood located in the electroporation chamber in order to kill the at least one CTC; and controlling a pump arrangement to pump the electric-field-applied-circulating blood back into the body, wherein the computer arrangement is further configured to directly apply the electric field to the blood on tubing located in the CTC treatment arrangement in order to kill the at least one CTC.

17. The computer-accessible medium of claim 16, wherein the control of the pumping of the blood from the body performed by controlling the pump arrangement.

18. The computer-accessible medium of claim 17, wherein the pump arrangement includes a peristaltic pump.

19. The computer-accessible medium of claim 16, wherein the computer arrangement is further configured to:

control pumping further blood from the body to the electroporation chamber;

control an application of a further electric field to the further blood located in the electroporation chamber in order to kill at least one further CTC; and control the pump arrangement to pump the further electric field-applied blood back into the body.

20. The computer-accessible medium of claim 16, wherein the electric field includes a plurality of micro pulses.

21. The computer-accessible medium of claim 16, wherein the electroporation chamber includes at least one of (i) a plurality of electrodes electrically connected to a field generator, or (ii) an input port and an output port.

22. A system for killing at least one circulating tumor cell (CTC), comprising:

a computer hardware arrangement specifically configured to:

control pumping of blood from a body of a patient to an electroporation chamber inside of a CTC treatment arrangement to circulate the blood;

control an application of an electric field to the circulating blood located in the electroporation chamber in order to kill the at least one CTC; and control a pump arrangement to pump of the electric-field-applied-circulating blood back into the body, wherein the computer hardware arrangement is further configured to control a direct application of the electric field to the blood on tubing located in the CTC treatment arrangement in order to kill the at least one CTC.

23. The system of claim 22, wherein the pumping of the blood from the body is performed using the pump arrangement.

24. The system of claim 23, wherein the pump arrangement includes a peristaltic pump.

25. The system of claim 22, wherein the computer hardware arrangement is further configured to:

control pumping of further blood from the body to the electroporation chamber;

apply a further electric field to the further blood located in the electroporation chamber in order to kill at least one further CTC; and control the pump arrangement to pump of the further electric field-applied blood back into the body.

26. The system of claim 22, wherein the electric field includes a plurality of micro pulses.

27. The system of claim 22, wherein the electroporation chamber includes at least one (i) a plurality of electrodes electrically connected to a field generator, or (ii) an input port and an output port.

\* \* \* \* \*